US012685664B2

(12) United States Patent
Shin

(10) Patent No.: US 12,685,664 B2
(45) Date of Patent: Jul. 21, 2026

(54) MANDIBULAR ADVANCEMENT FRAME AND MANDIBULAR ADVANCEMENT APPARATUS COMPRISING SAME

(71) Applicant: SEOUL NATIONAL UNIVERSITY R&DB FOUNDATION, Seoul (KR)

(72) Inventor: Hyunwoo Shin, Gyeonggi-do (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 404 days.

(21) Appl. No.: 18/021,259

(22) PCT Filed: Jul. 29, 2021

(86) PCT No.: PCT/KR2021/009848
§ 371 (c)(1),
(2) Date: Feb. 14, 2023

(87) PCT Pub. No.: WO2022/035098
PCT Pub. Date: Feb. 17, 2022

(65) Prior Publication Data
US 2024/0033123 A1     Feb. 1, 2024

(30) Foreign Application Priority Data
Aug. 14, 2020     (KR) ........................ 10-2020-0102510

(51) Int. Cl.
*A61C 7/08*          (2006.01)
*A61F 5/56*          (2006.01)
(52) U.S. Cl.
CPC .................................. *A61F 5/566* (2013.01)
(58) Field of Classification Search
CPC .... A61C 7/06; A61C 7/36; A61C 7/08; A61F 5/566

USPC ............................................................. 433/2
See application file for complete search history.

(56)                    References Cited

U.S. PATENT DOCUMENTS 4,602,905 A * 7/1986 O'Keefe, III ........ A61C 9/0006
                                                433/41
5,154,609 A * 10/1992 George ................ A61C 9/0006
                                                433/68
5,313,960 A * 5/1994 Tomasi ................... A61F 5/566
                                                128/862
(Continued)

FOREIGN PATENT DOCUMENTS

CA          3117315 A1     5/2019
JP      2012-528698 A     11/2012
(Continued)

OTHER PUBLICATIONS

International Search Report issued in corresponding International Patent Application No. PCT/KR2021/009848 dated Nov. 26, 2021.
(Continued)

*Primary Examiner* — Matthew M Nelson
(74) *Attorney, Agent, or Firm* — Morgan, Lewis & Bockius LLP

(57)                    ABSTRACT

A mandibular advancement frame includes a support portion for supporting a side surface of an intraoral device, and a connection portion connected to the support portion and inclined at an angle set in advance with respect to the support portion, wherein a plurality of through holes are provided in at least one of the support portion and the connection portion.

19 Claims, 7 Drawing Sheets

(56) References Cited

U.S. PATENT DOCUMENTS

| 5,678,567 | A | * | 10/1997 | Thornton | A61F 5/566 |
| | | | | | 128/848 |
| 5,794,627 | A | * | 8/1998 | Frantz | A61F 5/566 |
| | | | | | 128/859 |
| 5,846,212 | A | * | 12/1998 | Beeuwkes, III | A61H 1/00 |
| | | | | | 482/11 |
| 6,170,485 | B1 | * | 1/2001 | Orrico | A61F 5/566 |
| | | | | | 128/862 |
| 6,305,376 | B1 | * | 10/2001 | Thornton | A61F 5/566 |
| | | | | | 128/846 |
| 7,832,403 | B2 | * | 11/2010 | Halstrom | A61F 5/566 |
| | | | | | 128/848 |
| 10,251,729 | B1 | * | 4/2019 | Raslambekov | A61C 7/36 |
| 10,709,599 | B2 | * | 7/2020 | Remmers | A61F 5/56 |
| 2005/0028827 | A1 | * | 2/2005 | Halstrom | A61F 5/566 |
| | | | | | 128/848 |
| 2010/0300457 | A1 | * | 12/2010 | Horchover | A61F 5/56 |
| | | | | | 128/898 |
| 2010/0316973 | A1 | * | 12/2010 | Remmers | A61F 5/566 |
| | | | | | 433/214 |
| 2011/0232652 | A1 | * | 9/2011 | Levendowski | A61F 5/566 |
| | | | | | 128/848 |
| 2013/0023797 | A1 | * | 1/2013 | Hanewinkel | A61B 5/1121 |
| | | | | | 29/428 |
| 2014/0114146 | A1 | * | 4/2014 | Hanewinkel | A61B 5/4552 |
| | | | | | 600/301 |
| 2015/0164682 | A1 | * | 6/2015 | Remmers | A61B 5/4836 |
| | | | | | 600/529 |
| 2017/0049607 | A1 | * | 2/2017 | Thornton | A61C 7/36 |
| 2017/0135849 | A1 | | 5/2017 | Oowa et al. | |
| 2020/0121494 | A1 | | 4/2020 | Kusukawa et al. | |
| 2024/0033123 | A1 | * | 2/2024 | Shin | A61F 5/566 |

FOREIGN PATENT DOCUMENTS

| JP | 2017-506929 A | 3/2017 |
| JP | 2017-086591 A | 5/2017 |
| KR | 10-2011-0125491 A | 11/2011 |
| KR | 10-1235888 B1 | 2/2013 |
| KR | 10-1784416 B1 | 11/2017 |
| WO | 2019/094744 A1 | 5/2019 |
| WO | 2019/173869 A1 | 9/2019 |

OTHER PUBLICATIONS

Extended European Search Report issued in corresponding European Patent Application No. 21856104.1, dated Dec. 14, 2023.
Office Action issued in corresponding European Patent Application No. 21856104.1, dated Oct. 11, 2024.
Office Action issued in corresponding European Patent Application No. 21856104.1, dated Oct. 2, 2025.

* cited by examiner

MANDIBULAR ADVANCEMENT FRAME AND MANDIBULAR ADVANCEMENT APPARATUS COMPRISING SAME

The present disclosure relates to an apparatus, and in detail, the present disclosure relates to a mandibular advancement frame and a mandibular advancement apparatus including the same.

BACKGROUND ART

Sleep apnea is a type of sleep breathing disorder in which breathing stops due to obstruction of upper airway during sleep, and is a very common disease with a prevalence of 27% in men and 16% in women. In order to treat such sleep apnea, a mandibular forward movement apparatus capable of widening a space of the airway is widely used. The mandibular forward movement apparatus is attached to upper and lower teeth like a mouthpiece, and by forcibly moving the mandibulae forward, that is, in the opposite direction of the airway, by a predetermined length, thereby pulling tissue of tongue or airway forward in a supine position to increase airway space.

DESCRIPTION OF EMBODIMENTS

Technical Problem

The purpose of the present disclosure is to provide a mandibular advancement frame that may effectively deliver driving forces to an intraoral device.

Technical Solution to Problem

In order to achieve the above object, the mandibular advancement frame according to one embodiment of the present disclosure includes a support portion for supporting a side surface of an intraoral device, and a connection portion connected to the support portion and inclined at an angle set in advance with respect to the support portion, wherein a plurality of through holes may be provided in at least one of the support portion and the connection portion.

Advantageous Effects of Disclosure

A mandibular advancement frame and a mandibular advancement apparatus including the same according to embodiments of the present disclosure may minimize weight of the mandibular advancement frame by having a plurality of through holes, and may prevent a center of gravity of the mandibular advancement frame from deflecting in one direction by controlling sizes of the plurality of through holes. In addition, power may be transmitted to an intraoral device while minimizing volume of the mandibular advancement frame as a support portion and a connection portion are connected in an inclined state at a predetermined angle.

MODE OF DISCLOSURE

Figure 1:
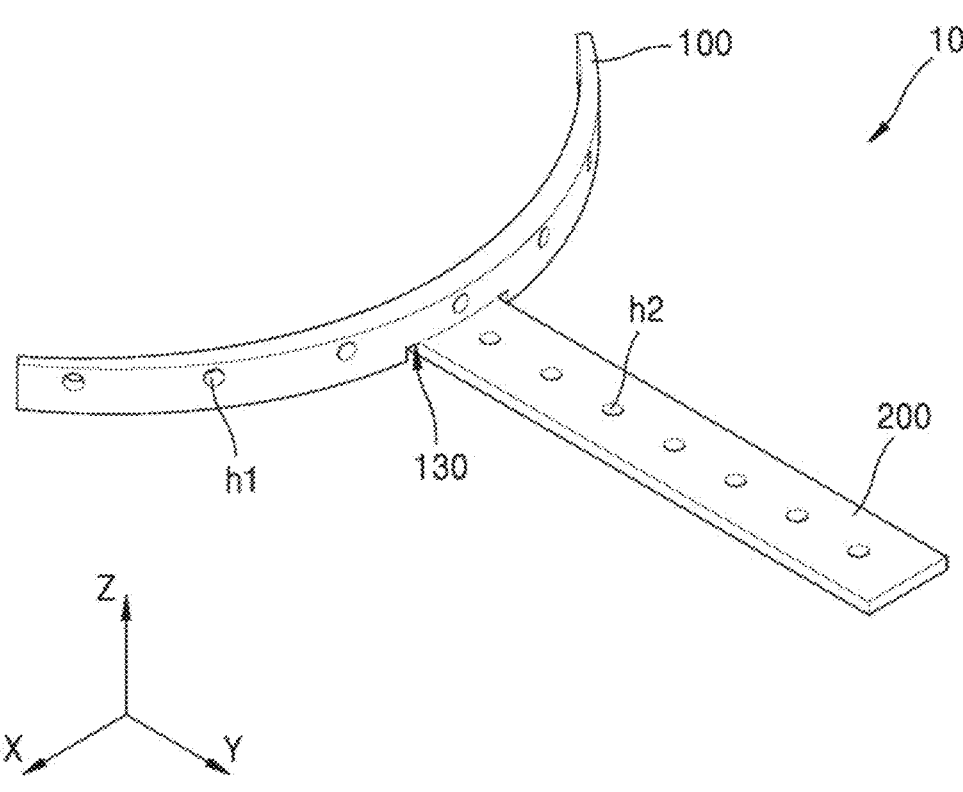
FIG. 1 is a perspective view illustrating a mandibular advancement frame according to an embodiment of the present disclosure.

The mandibular advancement frame according to one embodiment of the present disclosure includes a support portion for supporting a side surface of an intraoral device, and a connection portion connected to the support portion and inclined at an angle set in advance with respect to the support portion, wherein a plurality of through holes may be provided in at least one of the support portion and the connection portion.

In one embodiment of present disclosure, a bottom surface of the connection portion may be disposed on the same plane as a bottom surface of the support portion.

In one embodiment of present disclosure, a thickness of the support portion may vary along a direction in which the support portion extends.

In one embodiment of present disclosure, the thickness of the support portion may decrease from a center to a periphery of the support portion.

In one embodiment of the present disclosure, the connection portion may be inclined at 90° with respect to the support portion.

In one embodiment of present disclosure, the plurality of through holes may be spaced apart from each other in entire surfaces of the support portion and the connection portion.

In one embodiment of present disclosure, the plurality of through holes may have diameters of different sizes.

A mandibular advancement apparatus according to an embodiment of the present disclosure includes an upper teeth seating portion in which an user's upper teeth are seated, a lower seating portion in which lower teeth of the user are seated, a mandibular advancement frame connected to the upper teeth seating portion or the lower seating portion, and a driving unit connected to the mandibular advancement frame and changing a relative position of the lower seating portion with respect to the upper teeth seating portion, wherein the mandibular advancement frame includes a support portion supporting a side surface of the upper teeth seating portion or the lower seating portion and a connection portion connected to the support portion and inclined at an angle set in advance with respect to the support portion, and a plurality of through holes may be provided in at least one of the support portion and the connection portion.

MODE FOR INVENTION

Since the present disclosure may apply various transformations and may have various embodiments, specific embodiments are illustrated in the drawings and described in detail in the detailed description. However, this is not intended to limit the present disclosure to a specific embodiment, and it should be understood to include all transformations, equivalents, or substitutes included in the spirit and technical scope of the present disclosure. In describing the present disclosure, if it is determined that a detailed description of a related known technology may obscure the gist of the present disclosure, the detailed description will be omitted.

Terms such as first and second may be used to describe various components, but the components should not be limited by the terms. Terms are only used to distinguish one component from another.

Terms used in this application are only used to describe specific embodiments, and are not intended to limit the present disclosure. Singular expressions include plural expressions unless the context clearly dictates otherwise. In addition, in each drawing, components are exaggerated, omitted, or schematically illustrated for convenience and clarity of description, and the size of each component does not entirely reflect the actual size.

In the description of each component, what is described as being formed on or under includes both what is formed directly on or under or what is formed on or under through other components, and the criteria for on and under is described based on the drawings.

Hereinafter, an embodiment of the present disclosure will be described in detail with reference to the accompanying drawings, and in the description with reference to the accompanying drawings, the same or corresponding components are assigned the same reference numerals, and duplicate descriptions thereof will be omitted.

Figure 2:
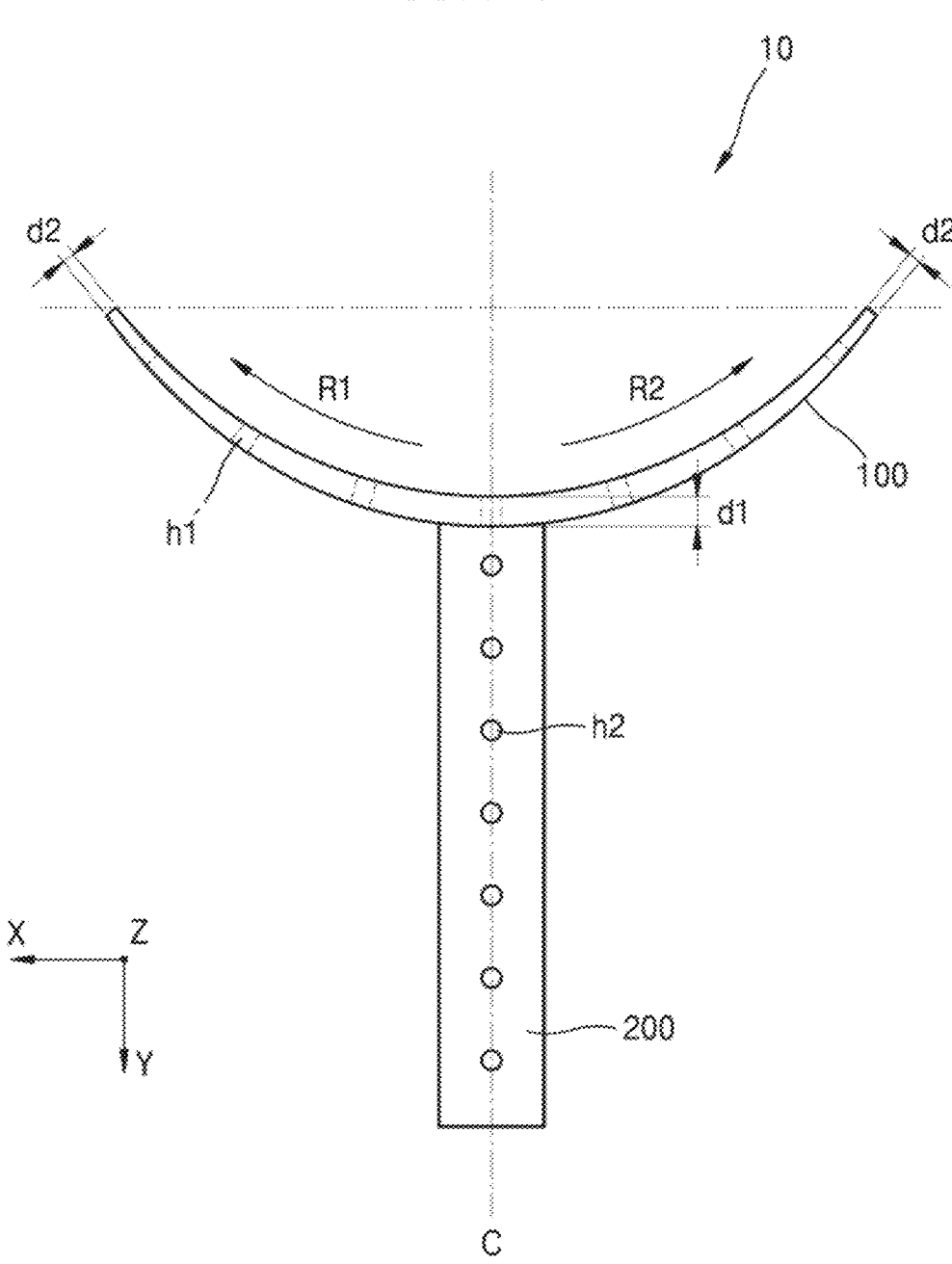
FIG. 2 is a plan view illustrating the mandibular advancement frame of FIG. 1.
Figure 3:
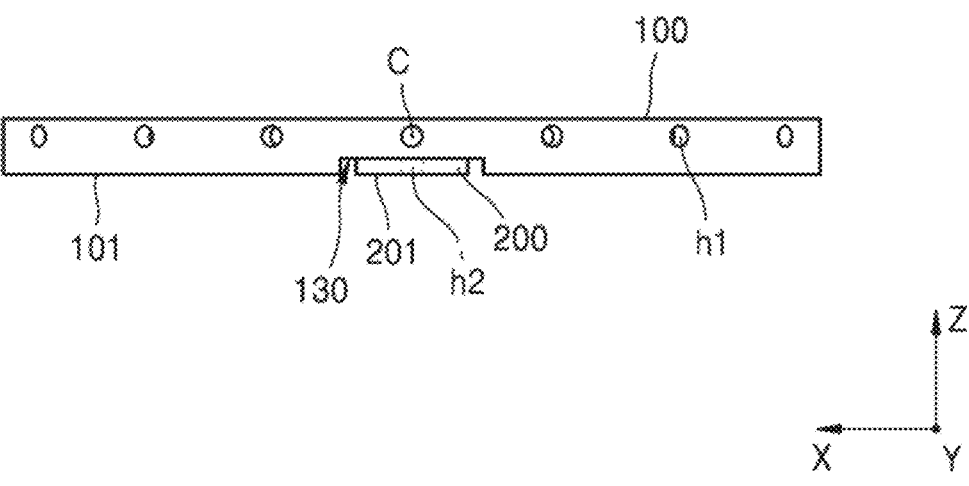
FIG. 3 is a front view illustrating the mandibular advancement frame of FIG. 1.
Figure 4:
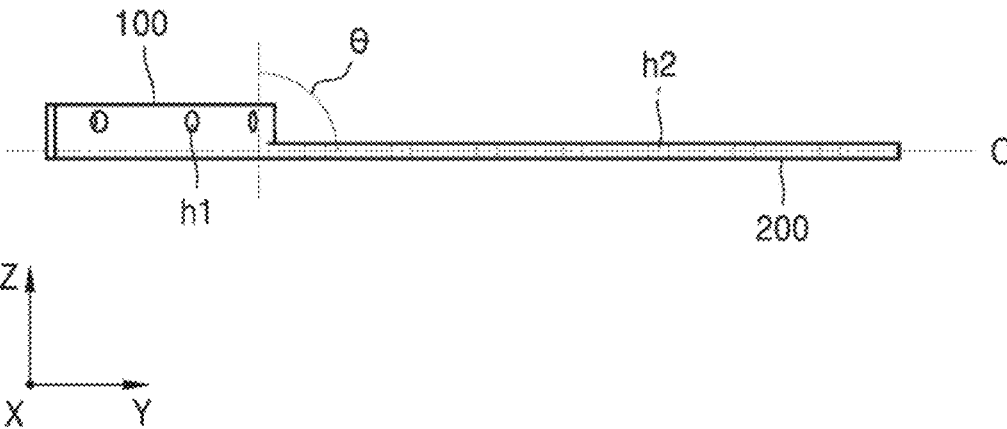
FIG. 4 is a cross-sectional view illustrating the mandibular advancement frame of FIG. 1.

FIG. 1 is a perspective view illustrating a mandibular advancement frame according to an embodiment of the present disclosure. FIG. 2 is a plan view illustrating the mandibular advancement frame of FIG. 1. FIG. 3 is a front view illustrating the mandibular advancement frame of FIG. 1, and FIG. 4 is a cross-sectional view illustrating the mandibular advancement frame of FIG. 1.

Referring to FIGS. 1 to 4, a mandibular advancement frame 10 may be a frame for delivering driving forces by being connected to an intraoral device provided in a mandibular advancement apparatus 1. At this time, the mandibular advancement frame 10 may include a support portion 100 and a connection portion 200. The support portion 100 and the connection portion 200 may be manufactured as an integral frame as a structure connected to one. For example, the mandibular advancement frame 10 may be manufactured as an integrally connected structure by forming the support portion 100 and the connection portion 200 with a plate formed of stainless alloys, titanium, titanium alloys, tungsten alloys, cobalt chromium alloys, and the like and bending the connection portion 200 with respect to the support portion 100. However, the present disclosure is not limited thereto, and the mandibular advancement frame 10 may be formed as the integral frame by injection molding with metal powders such as stainless alloy, titanium, titanium alloy, tungsten alloy, cobalt chromium alloy, and the like. Alternatively, the mandibular advancement frame 10 may be manufactured as a single frame by contacting the separately manufactured support portion 100 and the connection portion 200. Hereinafter, each component will be described in detail.

The support portion 100 may support the intraoral device, for example, an upper teeth seating portion 20 or a lower seating portion 30. Specifically, the support portion 100 may be connected to a side surface of the upper teeth seating portion 20 or the lower seating portion 30 to support the upper teeth seating portion 20 or the lower seating portion 30.

The support portion 100 may be a plate. As an example, the support portion 100 may be a plate curved with a predetermined curvature. In this case, the support portion 100 may be formed symmetrically around an imaginary center line C that is perpendicular to an imaginary line (for example, a line parallel to an X-axis direction in FIG. 2) connecting both ends of the support portion 100 and passes through a center of the support portion 100.

A first through hole h1 may be provided in the support portion 100. As an example, the first through hole h1 may be provided in plurality. In this case, the plurality of first through holes h1 may pass through the support portion 100 and be spaced apart from each other over an entire length of the support portion 100. As the plurality of first through holes h1 is formed in the support portion 100, the mandibular advancement frame 10 according to an embodiment of the present disclosure may reduce weight of the support portion 100 compared to a plate having the same volume and shape without a through hole.

The plurality of first through holes h1 may be arranged symmetrically about a center through hole, which is disposed at the center of the support portion 100 so that the center line C passes therethrough, of the plurality of first through holes h1. As a result, a center of gravity of the support portion 100 of the mandibular advancement frame 10 may not be biased to either side.

The plurality of first through holes h1 may be formed to have the same diameter as each other. In this case, the plurality of first through holes h1 having the same diameter are disposed on the support portion 100 so as to be symmetrical about the center through hole, so that the center of gravity of the support portion 100 and the mandibular advancement frame 10 including the same may not be biased in one direction.

However, the present disclosure is not limited to the above-described embodiment, and the plurality of first through holes h1 may be formed with different diameters. In this case, even when the support portion 100 is formed asymmetrically with respect to the center of the support portion 100, the entire center of gravity of the support portion 100 may not be deflected in one direction by forming the first through holes h1 in different sizes.

Specifically, the center of gravity of the mandibular advancement frame may be controlled by arranging large-diameter first through holes h1 in a portion formed with a longer length based on the center of the support portion 100 to equally adjust the weight of both sides. As a result, when both ends of the support portion 100 are not located on the same line or when it is necessary to form a specific portion of the support portion 100 with a different thickness than other portions, the mandibular advancement frame 10 adjusts the size of the plurality of first through holes h1 differently, so that the center of gravity of the support portion 100 and the mandibular advancement frame 10 may be located at the center of the support portion 100 and the mandibular advancement frame 100.

As an example, a thickness of the support portion 100 may vary along directions in which the support portion 100 extends (R1 direction and R2 direction). In this case, a thickness of the center of the support portion 100 (hereinafter, first thickness d1) may be different from a thickness of an end of the support portion 100 (hereinafter, second thickness d2).

Specifically, the support portion 100 has a maximum thickness [i.e., first thickness d1] at the center of the support portion 100, and the thickness may gradually decrease from the center of the support portion 100 toward the outer part along the R1 direction and from the center of the support portion 100 toward the outer part along the R2 direction. Accordingly, the support portion 100 may have a minimum thickness [i.e., second thickness d2] at both ends of the support portion 100.

As such, the thickness of the mandibular advancement frame 10 is maximized at the center of the support portion 100 to which the connection portion 200 is connected, thereby preventing bending or twisting of the support portion 100 due to driving forces generated by a driving unit 40 and stably delivering the driving forces to the support portion 100. In addition, the support portion 100 is formed so that the thickness becomes thinner toward the outer portion to which the connection portion 200 is not directly connected, thereby reducing the weight and volume of the mandibular advancement frame 10.

However, the present disclosure is not limited to the above-described embodiment, and as another embodiment, the support portion 100 may be formed with the same thickness from the center to both ends of the support portion 100, that is, throughout the length of the support portion 100.

Referring to FIGS. 3 and 4, the support portion 100 may include a processing portion 130. In this case, the processing portion 130 may be disposed on a lower surface of the support portion 100 and formed concavely from the lower surface of the support portion 100 toward an upper surface of the support portion 100. The processing portion 130 may be formed at a location where the support portion 100 and the connection portion 200 are connected. In the process of bending the connection portion 200 from the support portion 100, the processing portion 130 may be formed by processing such as cutting so that the connection portion 200 is easily bent.

The processing portion 130 may be disposed in a center of the lower surface of the support portion 100. Specifically, the processing portion 130 may be arranged symmetrically about the center line C. Accordingly, the center of gravity of the support portion 100 may be located at the center of the support portion 100 even when the processing portion 130 is provided.

The connection portion 200 may transfer the driving forces generated by the driving unit 40 to the support portion 100, and thus the driving forces may be transferred to the upper teeth seating portion 20 and the lower seating portion 30 coupled to the support portion 100. In this case, the connection portion 200 may have various shapes such as a cylinder or a polygonal shape, but for convenience of description, an embodiment in which the connection portion 200 is a rectangular parallelepiped plate will be mainly described below.

One end of the connection portion 200 may be connected to the support portion 100, and the other end may extend toward an outside of the support portion 100. At this time, the connection portion 200 may be inclined at an angle θ set in advance with respect to the support portion 100. Specifically, one end of the connection portion 200 is connected to the support portion 100, and the other end of the connection portion 200 may be extended to be inclined at the angle θ set in advance with respect to a width direction (e.g., Z-axis direction) of the support portion 100. For example, the angle θ set in advance may be formed at 80 to 100°, so that the connection portion 200 may extend in a direction (Y-axis direction) perpendicular to the width direction (Z-axis direction) of the support portion 100. Thereby, the mandibular advancement frame 10 may reduce the volume of the mandibular advancement frame 10 in a height direction (Z-axis direction).

As an example, the connection portion 200 may be connected to the processing portion 130 provided in the support portion 100. In this case, one end of the connection portion 200 may be connected to the inside of the processing portion 130, and the other end of the connection portion 200 may extend toward the outside of the support portion 100. In this case, a thickness of the connection portion 200 in the Z-axis direction may be the same as a depth of the processing portion 130 in the Z-axis direction. Accordingly, a bottom surface 201 of the connection portion 200 and a bottom surface 101 of the support portion 100 are located on the same plane, so that the bottom surface 201 of the connection portion 200 may not protrude to the outside the processing portion 130. As a result, the volume of the mandibular advancement frame 10 in the height direction (Z-axis direction) may be minimized.

A second through hole h2 may be provided in the connection portion 200. As an example, the second through hole h2 may be provided in plurality. In this case, the plurality of second through holes h2 may pass through the connection portion 200 and be spaced apart from each other over the entire length of the connection portion 200. As such, since the plurality of second through holes h2 is formed in the connection portion 200, the mandibular advancement frame 10 may reduce a weight of the connection portion 200 compared to a plate having the same volume and shape without through holes.

The plurality of second through holes h2 may be arranged in a row on the connection portion 200. Specifically, the plurality of second through holes h2 may be arranged in a line along the center line C of the connection portion 200. As a result, a center of gravity of the connection portion 200 may not be biased to either side. In this case, diameters of the plurality of second through holes h2 may be the same or the diameters of the plurality of second through holes h2 may be different from each other, which is the same as or similar to the above-described first through hole h1, so a detailed description thereof will be omitted.

As described above, by forming the first through hole h1 and the second through hole h2 in the support portion 100 and the connection portion 200, the weight of the mandibular advancement frame 10 may be minimized while maintaining the overall shape of the mandibular advancement frame 10.

Figure 5:
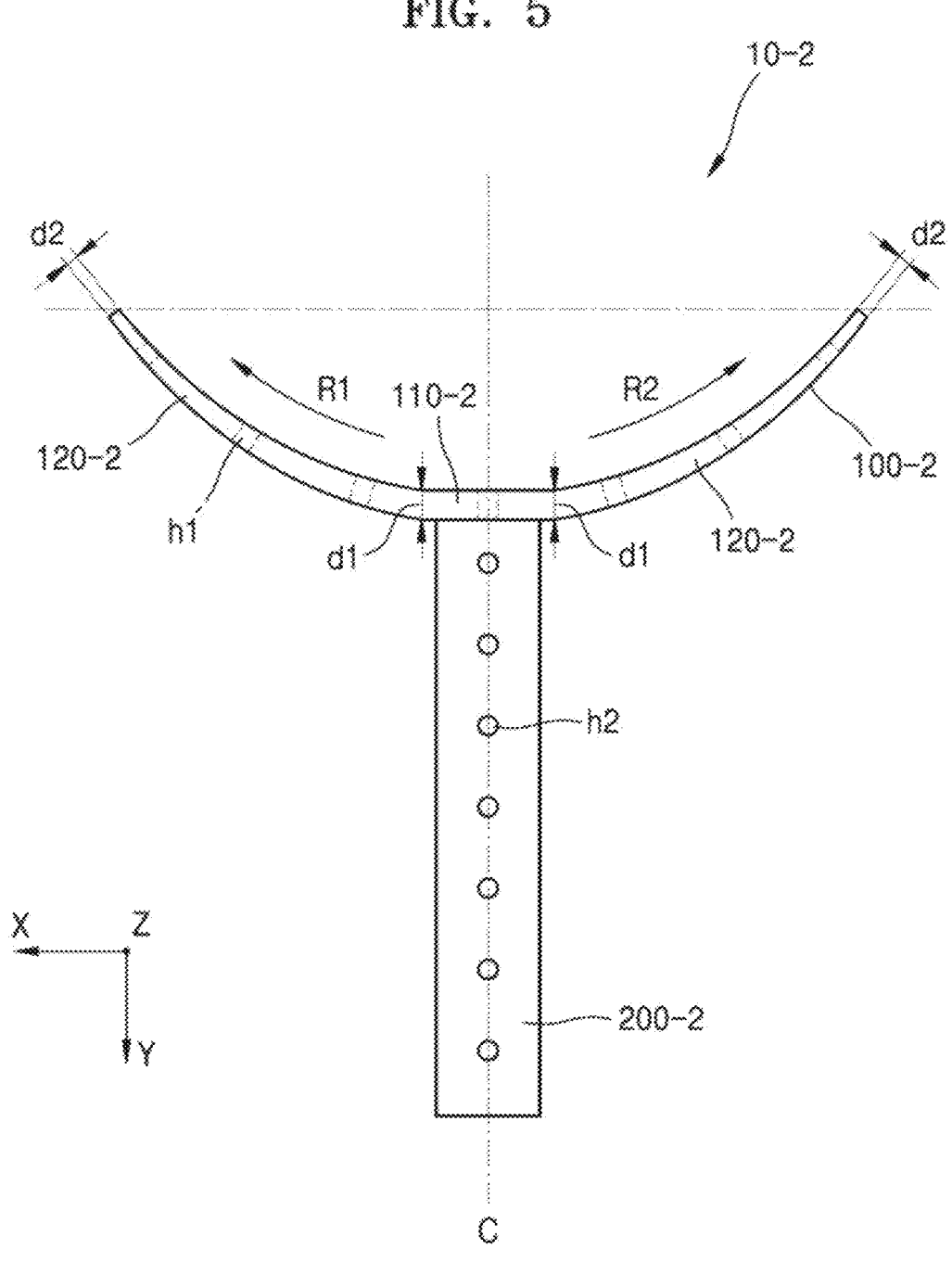
FIG. 5 is a plan view illustrating a mandibular advancement frame according to another embodiment of the present disclosure.

FIG. 5 is a plan view illustrating a mandibular advancement frame according to another embodiment of the present disclosure.

Referring to FIG. 5, a mandibular advancement frame 10-2 may include a support portion 100-2 and a connection portion 200-2. At this time, since specific features of the connection portion 200-2 are the same as or similar to those described above, overlapping descriptions thereof will be omitted and will be described focusing on differences from the above-described embodiment.

The support portion 100-2 may be connected to a side surface of an upper teeth seating portion 20 or a lower seating portion 30 to support the upper teeth seating portion 20 or the lower seating portion 30. In this case, the support portion 100-2 may include a straight portion 110-2 and a curved portion 120-2.

The straight portion 110-2 is disposed in a center of the support portion 100 and may extend in a direction parallel to a width direction (X-axis direction) of the connection portion 200. At this time, the connection portion 200-2 is connected to the straight portion 110-2, and a center of the straight portion 110-2 may coincide with a center of the support portion 100. Specifically, the connection portion 200 may be connected to one end of the straight portion 110-2 and may extend along an Y-axis direction parallel to a center line C passing through the center of the straight portion 110-2 and perpendicular to a longitudinal direction (X-axis direction) of the straight portion 110-2. Accordingly, the straight portion 110-2 or the support portion 100 may be disposed symmetrically around the connection portion 200, so that the connection portion 200 may be placed such that the center line C of the connection portion 200 passes through a center of gravity of the support portion 100.

Although not illustrated in the drawing, the straight portion 110-2 may have a processing portion (not illustrated) similarly to the embodiment described in FIG. 3 [i.e., mandibular advancement frame 10]. In this case, the processing portion is disposed on a lower surface of the straight portion 110-2 and may be concave from the lower surface of the straight portion 110-2 toward an upper surface of the straight portion 110-2. At this time, a cross-sectional shape of the processing portion 130 viewed from an XZ plane is a rectangular shape, and the connection portion 200 may be connected to the processing portion, the same as described above.

The curved portion 120-2 may be connected to the straight portion 110-2. In this case, the curved portion 120-2 may be provided as a pair. In this case, the pair of curved portions 120-2 may be connected to both ends of the straight portion 110-2, respectively, and arranged symmetrically about the straight portion 110-2. Specifically, any one of the pair of curved portions 120-2 may be connected to one end of the straight portion 110-2 and may be curvedly extended along the R1 direction from one end of the straight portion 110-2. In addition, the other one of the pair of curved portions 120-2 is connected to the other end of the straight portion 110-2, and may be curvedly extended along the R2 direction from the other end of the straight portion 110-2. At this time, radii of curvature of the pair of curved portions 120-2 may be the same.

The straight portion 110-2 may have a constant first thickness d1 along the longitudinal direction (X-axis direction) of the straight portion 110-2. At this time, among the ends of the curved portion 120-2, the end connected to the straight portion 110-2 is formed with the same first thickness d1 as the straight portion 110-2, as the thickness gradually decreases along the R1 direction from the straight portion 110-2 and along the R2 direction from the straight portion 110-2, both ends of the curved portion 120-2 may have a second thickness d2 thinner than the first thickness d1. That is, the support portion 100-2 has a maximum thickness [i.e., first thickness d1] at the straight portion 110-2 and the end of the curved portion 120-2 connected to the straight portion 110-2, and may have a minimum thickness [i.e., second thickness d2] at the end of the curved portion 120-2.

In the case described above, the straight portion 110-2 connected to the connection portion 200 has the maximum thickness d1 along its longitudinal direction (X-axis direction), so that the driving forces generated by the driving unit 40 may be reliably delivered to the support portion 100. In addition, the thickness of the curved portion 120-2 to which the connection portion 200 is not connected decreases along the extension directions (R1 and R2 directions), thereby reducing the volume and weight of the support portion 100.

Figure 6:
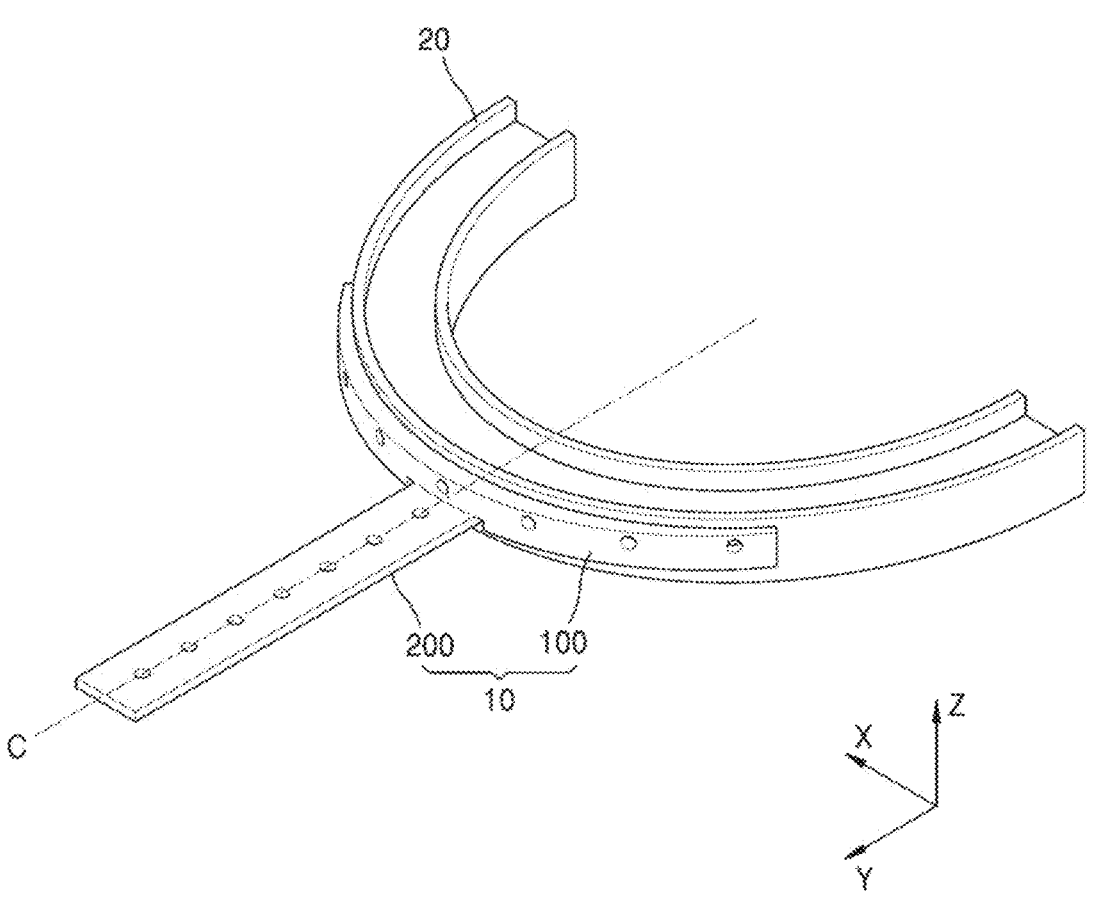
FIG. 6 is a perspective view illustrating a state in which an upper teeth seating portion is coupled to a mandibular advancement frame according to an embodiment of the present disclosure.
Figure 7:
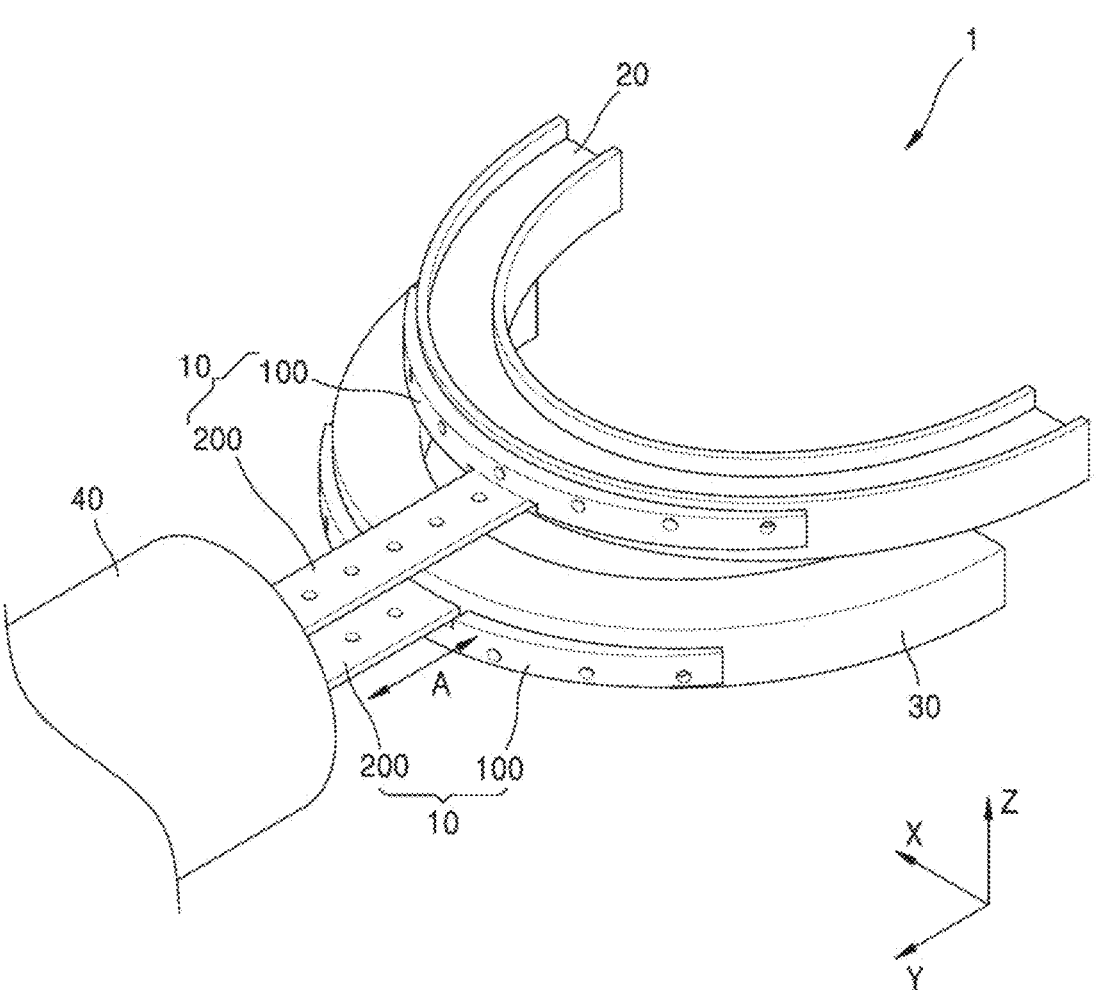
FIG. 7 is a perspective view illustrating a mandibular advancement apparatus according to an embodiment of the present disclosure.

FIG. 6 is a perspective view illustrating a state in which an upper teeth seating portion is coupled to a mandibular advancement frame according to an embodiment of the present disclosure, and FIG. 7 is a perspective view illustrating a mandibular advancement apparatus according to an embodiment of the present disclosure.

Referring to FIGS. 6 and 7, the mandibular advancement apparatus 1 may include the upper teeth seating portion 20, the lower seating portion 30, the mandibular advancement frame 10 and the driving unit 40.

As described above, the upper teeth seating portion 20 may seat the users upper teeth. The upper teeth seating portion 20 may be formed into a shape into which the user's upper teeth may be inserted. The upper teeth seating portion 20 may be custom-made according to the user's teeth alignment in order to minimize foreign body sensation or discomfort when the upper teeth are seated. When the upper teeth seating portion 20 is worn on the upper teeth, it may surround the upper teeth and be in close contact with the upper teeth.

As described above, the lower seating portion 30 may seat the user's lower teeth. The lower seating portion 30 may be custom-made according to the user's teeth alignment in order to minimize foreign body sensation or discomfort when the lower teeth are seated. When the lower seating portion 30 is worn on the lower teeth, it may surround the lower teeth and be in close contact with the lower teeth.

The mandibular advancement frame 10 may be combined with the upper teeth seating portion 20 or the lower seating portion 30. Accordingly, the upper teeth seating portion 20 and the lower seating portion 30 may be supported by the mandibular advancement frame 10.

The mandibular advancement frame 10 may be present in a pair. In this case, as an embodiment, one of the pair of mandibular advancement frames 10 (hereinafter referred to as a first frame) may be connected to the upper teeth seating portion 20 to support the upper teeth seating portion 20. In addition, another one of the pair of mandibular advancement frames 10 (hereinafter referred to as a second frame) may be connected to the lower seating portion 30 to support the lower seating portion 30.

Specifically, in the first frame, one surface of the support portion 100 of the first frame may be combined with an outer surface of the upper teeth seating portion 20. At this time, as an embodiment, the support portion 100 and the upper teeth seating portion 20 may be coupled by an adhesive. However, as another embodiment, at least a portion of the support portion 100 may be combined in a manner buried in the upper teeth seating portion 20. In this case, a part of the upper teeth seating portion 20 is inserted and fixed into the plurality of first through holes h1 provided in the support portion 100, so that the first frame and the upper teeth seating portion 20 may be more firmly coupled.

Meanwhile, in the second frame, one surface of the support portion 100 of the second frame may be combined with an outer surface of the lower seating portion 30. At this time, as an embodiment, the support portion 100 and the lower seating portion 30 may be coupled by an adhesive. However, as another embodiment, at least a portion of the support portion 100 may be combined in a manner buried in the lower seating portion 30. In this case, a part of the lower seating portion 30 is inserted and fixed into the plurality of first through holes h1 provided in the support portion 100, so that the first frame and the lower seating portion 30 may be more firmly coupled.

In a state in which the first frame and the second frame are coupled to the upper teeth seating portion 20 and the lower seating portion 30, respectively, the first frame and the second frame may be spaced apart from each other by a predetermined distance and connected to the driving unit 40. Accordingly, when at least one of the first frame and the second frame moves along a direction A by the driving unit 40, the first frame and the second frame may not interfere with each other's movements.

The driving unit 40 is connected to the upper teeth seating portion 20 and the lower seating portion 30 to change a relative position of the lower seating portion 30 with respect to the upper teeth seating portion 20. The driving unit 40 may include a power unit (not illustrated) that provides driving forces and a power transmission unit (not illustrated) that transfers the driving forces generated from the power unit to the upper teeth seating portion 20 or the lower seating portion 30.

The power unit may apply any means for generating driving forces. For example, the power unit may generate driving forces by using any one of a motor, an actuator and a pump. As another example, the power unit may generate driving forces by using an electromagnet or a shape memory alloy.

The power transmission unit may include a transmission means corresponding to the type of power unit. As an example, when the power unit is the motor or actuator, the power transmission unit may include one or more gears capable of transmitting driving forces generated from the motor or actuator. As another embodiment, when the power unit is the pump, the power transmission unit may include a cylinder and a piston to transfer a flow of air generated from the pump.

The mandibular advancement apparatus 1 may move the lower seating portion 30 to the direction A in FIG. 7 according to the user's sleep state (e.g., snoring and sleep apnea) or sleeping posture. As an example, when snoring and sleep apnea occur during sleep, the mandibular advancement apparatus 1 may drive the driving unit 40 to move the lower seating portion 30 forward so that the mandibulae protrude. As another embodiment, when the user has a supine sleeping posture, the mandibular advancement apparatus 1 may drive the driving unit 40 to move the lower seating portion 30 forward, subsequently, when the user changes the sleeping posture from a supine position to a lateral position or the prone position, the mandibular advancement apparatus 1 may drive the driving unit to return the lower seating portion 30 to an initial position relative to the upper teeth seating portion 20.

As such, an airway near a pharynx is maintained in an open state by the forwardly moved lower seating portion 30, and the airway is expanded, so that a flow of air in the airway may be smooth. As a result, snoring and sleep apnea symptoms during sleep may be alleviated.

As described above, the mandibular advancement frame 10 and 10-2 according to the embodiments of the present disclosure and the mandibular advancement apparatus 1 including the same include the plurality of through holes h1 and h2, so that the weight of the mandibular advancement frame 10 may be minimized, and the center of gravity of the mandibular advancement frame 10 may be prevented from being deflected in one direction by adjusting the sizes of the plurality of through holes h1 and h2. In addition, since the support portion 100 and the connection portion 200 are connected in the inclined state at the predetermined angle, power may be transmitted to the intraoral device while minimizing the volume of the mandibular advancement frame 10.

Although the above has been described with reference to the embodiments shown in the drawings, this is only exemplary, and those skilled in the art will understand that various modifications and equivalent other embodiments are possible therefrom. Therefore, the true technical protection scope of the present disclosure should be determined by the technical spirit of the appended claims.

INDUSTRIAL APPLICABILITY

According to one embodiment of the present disclosure, a mandibular advancement frame and a mandibular advancement apparatus including the same are provided. In addition, the embodiments of the present disclosure may be applied to a mandibular advancement apparatus used industrially.

The invention claimed is:

1. A mandibular advancement frame comprising:
a support portion, separate from an intraoral device configured to receive a user's teeth, wherein the support portion has a curved plate shape extending along a dental-arch direction and configured solely to cover an outer side surface of the intraoral device corresponding to an opposite-tongue side surface among side surfaces of the user's teeth and is configured to be joined in surface contact with the outer side surface of the intraoral device to support the intraoral device; and
a connection portion integrated with the support portion and inclined at an angle set in advance with respect to the support portion, the connection portion having a bottom surface parallel to a lower surface of the support portion and a first thickness in a normal direction of the bottom surface and adjacent to the support portion; and
a processing portion provided concavely from the lower surface of the support portion toward an upper surface thereof by a first depth, the processing portion located at a central region of the lower surface of the support portion and at a junction where the support portion and the connection portion are connected,
wherein a plurality of through holes are provided in at least one of the support portion and the connection portion, and
wherein the first thickness of the connection portion and the first depth of the processing portion are equal.

2. The mandibular advancement frame of claim 1, wherein the connection portion is connected to a center of the support portion.

3. The mandibular advancement frame of claim 1, wherein the bottom surface of the connection portion is disposed on the same plane as a bottom surface of the support portion.

4. The mandibular advancement frame of claim 1, wherein a thickness of the support portion varies along a direction in which the support portion extends.

5. The mandibular advancement frame of claim 4, wherein the support portion has a maximum thickness at a central region where the connection portion is connected, and has a minimum thickness at opposite ends away from the connection portion.

6. The mandibular advancement frame of claim 1, wherein the connection portion is inclined at an angle selected from 80° to 100° with respect to the support portion.

7. The mandibular advancement frame of claim 1, wherein the plurality of through holes including first and second through holes are spaced apart from each other in entire surfaces of the support portion and the connection portion.

8. The mandibular advancement frame of claim 7, wherein the plurality of second through holes formed in the connection portion are arranged linearly along a centerline parallel to a longitudinal direction of the connection portion.

9. The mandibular advancement frame of claim 8, wherein the second through holes in the connection portion and the first through holes in the support portion have the same diameter.

10. The mandibular advancement frame of claim 1, wherein the plurality of through holes have diameters of different sizes.

11. The mandibular advancement frame of claim 1, wherein the support portion and the connection portion constitute a single structural body.

12. The mandibular advancement frame of claim 1, wherein the curved plate shape of the support has a predetermined curvature of a semicircular shape.

13. A mandibular advancement system comprising:
an upper teeth seating portion in which a user's upper teeth are seated;
a lower seating portion in which lower teeth of the user are seated;
a first mandibular advancement frame configured to be attached to the upper teeth seating portion and a second mandibular advancement frame configured to be attached to the lower seating portion; and
a driving unit connected to the first and second mandibular advancement frames and changing a relative position of the lower seating portion with respect to the upper teeth seating portion by moving at least one of the first and second mandibular advancement frames,
wherein each of the first and second mandibular advancement frames includes:
a support portion, separate from the upper and lower teeth seating portions, having a curved plate shape extending along a dental-arch direction and configured solely to cover an outer side surface of the upper and lower teeth seating portions and configured to be joined in surface contact with the outer side surface of the upper and lower teeth seating portions for supporting a side surface of the upper teeth seating portion and the lower seating portion; and
a connection portion integrated with the support portion and inclined at an angle set in advance with respect to the support portion, the connection portion having a bottom surface parallel to a lower surface of the support portion and a first thickness in a normal direction of the bottom surface and adjacent to the support portion; and
a processing portion provided concavely from the lower surface of the support portion toward an upper surface thereof by a first depth, the processing portion located at a central region of the lower surface of the support portion and at a junction where the support portion and the connection portion are connected,
wherein a plurality of through holes are provided in at least one of the support portion and the connection portion, and
wherein the first thickness of the connection portion and the first depth of the processing portion are equal.

14. The mandibular advancement system of claim 13, wherein the curved plate shape of the support has a predetermined curvature of a semicircular shape.

15. A mandibular advancement apparatus comprising:
a first mandibular advancement frame configured to be selectively attached to an upper teeth seating portion;
a second mandibular advancement frame configured to be selectively attached to a lower seating portion; and
a driving unit connected to the first and second mandibular advancement frames and changing a relative position of one of the upper and lower seating portions with respect to another of the upper and lower teeth seating portions by moving at least one of the first and second mandibular advancement frames,
wherein each of the first and second mandibular advancement frames includes:
a support portion, separate from the upper and lower teeth seating portions, having a curved plate shape extending along a dental-arch direction and configured solely to cover an outer side surface of the upper and lower teeth seating portions by being selectively joined in surface contact with the outer side surface of the upper and lower teeth seating portions for supporting a side surface of the upper teeth seating portion and the lower seating portion; and
a connection portion integrated with the support portion and inclined at an angle set in advance with respect to the support portion, the connection portion having a bottom surface parallel to a lower surface of the support portion and a first thickness in a normal direction of the bottom surface and adjacent to the support portion; and
a processing portion provided concavely from the lower surface of the support portion toward an upper surface thereof by a first depth, the processing portion located at a central region of the lower surface of the support portion and at a junction where the support portion and the connection portion are connected,
wherein the curved plate shape of the support has a predetermined curvature of a semicircular shape, and
wherein the first thickness of the connection portion and the first depth of the processing portion are equal.

16. The mandibular advancement frame of claim 15, wherein the processing portion is formed by cutting to improve bendability of the connection portion when the connection portion is bent from the support portion.

17. The mandibular advancement frame of claim 16, wherein the processing portion is disposed on the lower surface of the support portion and is centrally aligned to maintain the center of gravity of the support portion despite presence of the processing portion.

18. The mandibular advancement frame of claim 15, wherein a height of the processing portion is equal to a thickness of the connection portion.

19. The mandibular advancement frame of claim 18, wherein a width of the processing portion is greater than a width of the connection portion.

* * * * *